United States Patent
Schiffmann et al.

(10) Patent No.: US 9,750,732 B2
(45) Date of Patent: Sep. 5, 2017

(54) URINARY TRIAOSYLCERAMIDE (GB3) AS A MARKER OF CARDIAC DISEASE

(71) Applicant: Baylor Research Institute, Dallas, TX (US)

(72) Inventors: Raphael Schiffmann, Rockwall, TX (US); Fanny Mochel, Dallas, TX (US); Lawrence Sweetman, Heath, TX (US); Sabrina Forni, Dallas, TX (US)

(*) Notice: Subject to any disclaimer, the term of this patent is extended or adjusted under 35 U.S.C. 154(b) by 0 days.

(21) Appl. No.: 14/729,630

(22) Filed: Jun. 3, 2015

(65) Prior Publication Data
US 2015/0342939 A1     Dec. 3, 2015

Related U.S. Application Data

(62) Division of application No. 12/948,693, filed on Nov. 17, 2010, now Pat. No. 9,066,939.

(60) Provisional application No. 61/261,831, filed on Nov. 17, 2009.

(51) Int. Cl.
| | |
|---|---|
| *A61K 31/445* | (2006.01) |
| *A61B 10/00* | (2006.01) |
| *G01N 30/88* | (2006.01) |

(52) U.S. Cl.
CPC .......... *A61K 31/445* (2013.01); *A61B 10/007* (2013.01); *A61B 10/0051* (2013.01); *A61B 10/0058* (2013.01); *A61B 2010/0061* (2013.01); *G01N 2030/8831* (2013.01)

(58) Field of Classification Search
None
See application file for complete search history.

(56) References Cited

U.S. PATENT DOCUMENTS

2008/0056994 A1* 3/2008 Kaneski ............... A61K 31/45
424/9.2
2010/0266571 A1* 10/2010 Lockhart ............. A61K 31/445
424/94.62

* cited by examiner

*Primary Examiner* — Jeffrey S Lundgren
*Assistant Examiner* — Michael Schmitt
(74) *Attorney, Agent, or Firm* — Servilla Whitney LLC

(57) ABSTRACT

The present invention describes a method for determination of urinary globotriaosylceramide (Gb3) levels in non-Fabry disease cardiac patients. Determination of Gb3 levels provides a screening method for determining cardiac risk and may offer an alternative therapeutic option for cardiac disease management or cardiac disease risk mitigation by lowering Gb3 levels by the use of pharmacological chaperones or other agents.

7 Claims, 3 Drawing Sheets

URINARY TRIAOSYLCERAMIDE (GB3) AS A MARKER OF CARDIAC DISEASE

CROSS-REFERENCE TO RELATED APPLICATIONS

This application is a divisional application of U.S. patent application Ser. No. 12/948,693, filed Nov. 17, 2010, issued as U.S. Pat. No. 9,066,939, which claims priority to U.S. Provisional Patent Application No. 61/261,831, filed Nov. 17, 2009, the entire contents of both applications are hereby incorporated herein by reference in their entirety.

TECHNICAL FIELD OF THE INVENTION

The present invention relates in general to the field of cardiac disease markers, and more particularly to the detection of elevated urinary globotriaosylceramide (Gb3) levels in non-Fabry disease cardiac patients.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, its background is described in connection with the cardiac disease markers and methods of detection of Gb3 and other glycolipid markers in body fluids.

U.S. Pat. No. 7,445,886 issued to Grior et al. (2008) discloses a test for Macrophage migration inhibitory factor (MIF) a clinically useful biochemical marker of cardiovascular risk. Risk assessment includes the step of detecting in the blood of a person MIF concentration as a marker of cardiovascular risk for the person. The method of the '886 patent may further comprise the step of assigning to the person a cardiovascular risk metric proportional to the MIF concentration, and/or prescribing for the person a cardiovascular treatment modality in accordance with the MIF concentration. The method is useful as a primary screen, and may be used in conjunction with or as a substitute for additional tests, such as a stress test, CRP assay, LDL assay, etc. The detecting step may be repeated over time intervals and/or treatment to monitor change in cardiovascular risk for the person over time and/or treatment.

U.S. Patent Application No. 20040132688 (Griffin, et al., 2003) relates to plasma glucosylceramide deficiency as risk factor for thrombosis and modulator of anticoagulant protein C. According to Griffin, exogenously added glycosylceramide (GlcCer) and other neutral glycolipids such as the homologous Glc-containing globotriaosylceramide (Gb3Cer), dose-dependently prolonged clotting times of normal plasma in the presence but not absence of APC: protein S, indicating GlcCer or Gb3Cer can enhance protein C pathway anticoagulant activity. In studies using purified proteins, inactivation of factor Va by APC: protein S was enhanced by GlcCer alone and by GlcCer, globotriaosylceramide, lactosylceramide, and galactosylceramide in multicomponent vesicles containing phosphatidylserine and phosphatidylcholine. Thus, the Griffin invention provides neutral glycolipids such as GlcCer and Gb3Cer, as anticoagulant cofactors that contribute to the antithrombotic activity of the protein C pathway. The Griffin invention states that a deficiency of plasma GlcCer is a risk factor for thrombosis. Methods are provided to determine individuals at risk for thrombosis, methods of treatment as well as methods of screening for antithrombotic factors from neutral glycolipids.

SUMMARY OF THE INVENTION

The present invention describes a method for the determination of elevated level of urinary globotriaosylceramide (Gb3), a risk factor for cardiac disease in the general population. The Gb3 levels in the urine serve as a marker for cardiac disease. The method of the present invention provides a screening method for cardiac risk and implies that lower Gb3 levels may be beneficial in the treatment and management of the risk for cardiac disease.

In one embodiment the present invention provides a method of screening for the presence of a cardiac disease, a cardiac condition or a risk factor for cardiac diseases in a human subject by calculating levels of globotriaosylceramide (Gb3) in an urine sample comprising the steps of: (i) obtaining and placing the urine sample from the human subject on a filter paper, (ii) drying the urine sample placed on the filter paper, (iii) extracting the dried urine sample with methanol, (iv) injecting a portion of the extracted urine sample into a LC-MS system along with a radio-labeled standard solution comprising a known concentration of the Gb3 in methanol, (v) eluting the Gb3 in the urine sample and the standard solution with a methanol/water gradient, (vi) obtaining one or more peaks of the Gb3 in the urine sample and the standard solution in a mass spectrum from the LC-MS system, (vii) creating a calibration curve by plotting a peak area of the one or more peaks of Gb3 in the biological sample and the standard solutions against a retention time, (viii) calculating the level of the Gb3 in the urine sample from the calibration curve, and (ix) determining the presence of the cardiac disease, the cardiac condition or the risk factor for cardiac diseases if the level of the Gb3 in the urine sample is above a normal threshold value; wherein the normal threshold value is 200 ng/ml.

The method as described in the present invention further comprises the step of assigning a cardiac risk metric or prescribing a treatment regimen for the human subject based on a comparison of the level of Gb3 in the urine sample and the normal threshold value, wherein the cardiac risk metric is proportional to the level of the Gb3 in the urine sample of the human subject. In one aspect the cardiac disease or cardiac condition is selected from the group consisting of hypertrophic cardiomyopathy, rhythm and conduction defects, coronary artery disease, arrhythmia, conduction blocks, and valvular disease. In another aspect the human subject is a healthy human subject, a non-Fabry disease patient, a non-Fabry disease cardiac patient or a subject with no genetic predispositions towards Fabry's disease.

In another embodiment the present invention describes a pharmaceutical composition for treating a cardiac disease, a cardiac condition or for mitigating a risk factor for a cardiac condition in a human subject by reducing a level of globotriaosylceramide (Gb3) comprising: an active pharmacological or a chemical chaperone, wherein the pharmacological or a chemical chaperone comprises 1-deoxygalactonojirimycin (DGJ), 1-deoxygalactonojirimycin salts and derivatives, iminosugars and derivatives, deoxyazasugars and derivatives, calystegines alkaloids and derivatives, isofagomine, fagomine isomers, conduritol C epoxides, nortropane alkaloids, 4-phenylbutyrate, migalastat hydrochloride, molecules used in substrate reduction therapy[1], molecules used in correcting underlying epigenetic modifications associated with the increased Gb3 levels (i.e., HDAC inhibitors for acetylation modifications, modifications of phosphorylation sites by amino acids substitution), molecules affecting an expression and or a function of one or more modifier genes interacting with a gene encoding an α-galactosidase A or a synthetic gene of the Gb3 or its precursors such as Gb3 synthase (A4GAL7) or any combinations thereof and one or more optional pharmaceutically acceptable excipients.

In one aspect of the present invention the cardiac disease or cardiac condition is selected from the group consisting of hypertrophic cardiomyopathy, rhythm and conduction defects, coronary artery disease, arrhythmia, conduction blocks, and valvular disease. In another aspect the human subject is a healthy human subject, a non-Fabry disease patient, a non-Fabry disease cardiac patient or a subject with no genetic predispositions towards Fabry's disease.

The present invention further provides a method of treating a cardiac disease, a cardiac condition or for mitigating a risk factor for a cardiac condition in a human subject comprising the steps of, identifying a human subject in need for treatment against the cardiac disease, the cardiac condition or for mitigation of the risk factor for the cardiac condition and administering a pharmaceutical composition comprising an active pharmacological or a chemical chaperone, wherein the pharmacological or a chemical chaperone comprises 1-deoxygalactonojirimycin (DGJ), 1-deoxygalactonojirimycin salts and derivatives, iminosugars and derivatives, deoxyazasugars and derivatives, calystegines alkaloids and derivatives, isofagomine, fagomine isomers, conduritol C epoxides, nortropane alkaloids, 4-phenylbutyrate, migalastat hydrochloride, molecules used in substrate reduction therapy[1], molecules used in correcting underlying epigenetic modifications associated with the increased Gb3 levels (i.e., HDAC inhibitors for acetylation modifications, modifications of phosphorylation sites by amino acids substitution), molecules affecting an expression and or a function of one or more modifier genes interacting with a gene encoding an α-galactosidase A or a synthetic gene of the Gb3 or its precursors such as Gb3 synthase (A4GAL7) or any combinations thereof and one or more optional pharmaceutically acceptable excipients in a concentration sufficient to treat the cardiac disease, the cardiac condition or for the mitigation of the risk factor for the cardiac condition. The method of the present invention further comprises the step of monitoring a progress of the treatment against the cardiac disease, the cardiac condition or the mitigation of the risk factor for the cardiac condition by measuring a level of globotriaosylceramide (Gb3) in an urine sample from the human subject.

In one aspect of the method of the present invention a level of 200 ng/ml or lower of Gb3 in the urine sample is indicative of a successful treatment of the cardiac disease or the cardiac condition or of successful mitigation of the risk factor for the cardiac condition. In another aspect the cardiac disease or cardiac condition is selected from the group consisting of hypertrophic cardiomyopathy, rhythm and conduction defects, coronary artery disease, arrhythmia, conduction blocks, and valvular disease. In yet another aspect the human subject is a healthy human subject, a non-Fabry disease patient, a non-Fabry disease cardiac patient or a subject with no genetic predispositions towards Fabry's disease.

In one embodiment the present invention discloses a method of treating a cardiac disease, a cardiac condition or for mitigating a risk factor for a cardiac condition in a human subject comprising the steps of, identifying a human subject in need for treatment against the cardiac disease, the cardiac condition or for mitigation of the risk factor for the cardiac condition and administering a composition of migalastat hydrochloride and one or more optional pharmaceutically acceptable excipients in a concentration sufficient to treat the cardiac disease, the cardiac condition or for the mitigation of the risk factor for the cardiac condition. The method further comprises the step of monitoring a progress of the treatment against the cardiac disease, the cardiac condition or the mitigation of the risk factor for the cardiac condition by measuring a level of globotriaosylceramide (Gb3) in an urine sample from the human subject. In one aspect of the method of the present invention a level of 200 ng/ml or lower of Gb3 in the urine sample is indicative of a successful treatment of the cardiac disease or the cardiac condition or of successful mitigation of the risk factor for the cardiac condition. In another aspect the cardiac disease or cardiac condition is selected from the group consisting of hypertrophic cardiomyopathy, rhythm and conduction defects, coronary artery disease, arrhythmia, conduction blocks, and valvular disease.

The present invention further provides a method of detecting the presence of one or more glycolipids or glycosphingolipids in a biological sample from a human subject comprising the steps of: (i) obtaining and placing the biological sample from the human subject on a substrate, wherein the substrate is selected from the group consisting of a filter paper, a filter, a membrane, a bead, particle, an organic resin, a microtiter plate, and a slide, (ii) drying the biological sample placed on the substrate, (iii) extracting the dried biological sample with a suitable organic solvent, (iv) injecting a portion of the extracted biological sample into a LC-MS system along with a standard solution of known concentration of the glycolipid or the glycosphingolipid in the organic solvent, (v) eluting the glycolipid or the glycosphingolipid in the biological sample and the standard solution with a suitable solvent gradient, (vi) obtaining one or more peaks of the glycolipid or the glycosphingolipid in the biological sample and the standard solution in a mass spectrum from the LC-MS system, (vii) creating a calibration curve by plotting a peak area of the one or more peaks of the glycolipid or the glycosphingolipid in the biological sample and the standard solutions against a retention time, and (viii) detecting the presence of one or more glycolipids or glycosphingolipids in the biological sample by calculating a concentration of the one or more glycolipids or glycosphingolipids from the calibration curve.

In one aspect of the method of the present invention the one or more glycolipids or glycosphingolipids comprise globotriaosylceramide (Gb3), Globotriaosylsphingosine (Lyso-Gb3), lactosyl ceramide, galactosyl ceramide, glucosylceramide, neutral glycolipids or combinations thereof. In another aspect the biological sample is selected from the group consisting of plasma, stool, sputum, pancreatic fluid, bile, lymph, blood, urine, cerebrospinal fluid, seminal fluid, saliva, breast nipple aspirate, and pus. In specific aspects the glycosphingolipid is Gb3 and the biological sample is urine.

In yet another embodiment a method of detecting the presence of globotriaosylceramide (Gb3) in an urine sample from a human subject as described in the present comprises the steps of: obtaining and placing the urine sample from the human subject on a filter paper, drying the urine sample placed on the filter paper, extracting the dried urine sample with methanol, injecting a portion of the extracted urine sample into a LC-MS system along with a radio-labeled standard solution comprising a known concentration of the Gb3 in methanol, eluting the Gb3 in the urine sample and the standard solution with a methanol/water gradient, obtaining one or more peaks of the Gb3 in the urine sample and the standard solution in a mass spectrum from the LC-MS system, creating a calibration curve by plotting a peak area of the one or more peaks of Gb3 in the biological sample and the standard solutions against a retention time, and detecting the presence of the Gb3 in the urine sample by calculating a concentration of the Gb3 from the calibration curve.

The method of the present invention further comprises the step of screening for the presence of a cardiac disease, a cardiac condition or a risk factor for cardiac diseases by comparing the concentration of the Gb3 in the urine sample with a normal threshold value wherein the normal threshold value is 200 ng/ml. In one aspect a concentration of Gb3 greater than 200 ng/ml in the urine sample of the human subject is indicative of a cardiac disease, a cardiac condition or a risk factor for cardiac disease. In another aspect the cardiac disease or cardiac condition is selected from the group consisting of hypertrophic cardiomyopathy, rhythm and conduction defects, coronary artery disease, arrhythmia, conduction blocks, and valvular disease. In yet another aspect the human subject is a healthy human subject, a non-Fabry disease patient, a non-Fabry disease cardiac patient or a subject with no genetic predispositions towards Fabry's disease.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1A:
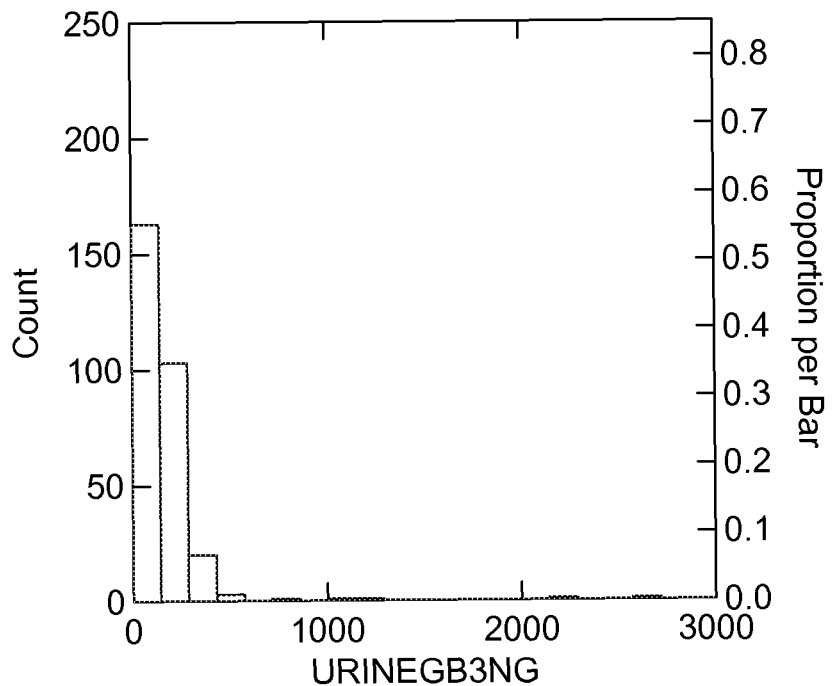
FIG. 1A is a graph showing the concentration distribution of Gb3 in all available urine specimens of cardiac patients enrolled in the study of the present invention (N=294). Cardiac patients data were analyzed with the software Systat and expressed as ng of Gb3/card (mL of urine)

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention describes the detection of elevated urinary Globotriaosylceramide (Gb3) levels, which is a risk factor for a variety of acquired cardiac abnormalities in the general population (non-Fabry diseased). This suggests the screening of high risk patients for cardiac disease by measuring urinary Gb3 levels. The present inventors suggest that lowering the Gb3 levels may be a way to lower the risk of cardiac disease in the non-Fabry general population. Gb3 levels can be lowered by pharmacological chaperones that are known to be able to increase wild type α-galactosidase A levels in cells or molecules that function as substrate reduction therapy or enzyme replacement therapy for patient with low α-galactosidase A levels. Presently, elevated urinary Gb3 has been associated exclusively with the genetic disorder called Fabry disease and has never been described in the general cardiac disease population.

Gb3 is a glycosphingolipid that accumulates in Fabry disease and is thought to be the main offending metabolite. Fabry disease is X-linked and is caused by a deficiency of lysosomal enzyme α-galactosidase A resulting in accumulation of Gb3 in all organs (particularly in heart and kidney) and many cell types and in the urine. This disease is associated particularly with a marked increased risk for stroke, cardiac disease (hypertrophic cardiomyopathy, rhythm and conduction defects, coronary artery disease and valvular abnormalities), and chronic proteinuric renal insufficiency. molecules that can correct the underlying epigenetic modification associated with the increased Gb3 levels (i.e. HDAC inhibitors for acetylation modifications, modifications of phosphorylation sites by amino acids substitution); and or molecules that can affect the expression and or function of modifier genes known to interact with the gene encoding α-galactosidase A or the synthetic genes of Gb3 or its precursors such as Gb3 synthase (A4GAL7).

Although Fabry disease is rare, the cardiac complications, progressive renal disease and stroke described above are similar in nature to those commonly seen in the general population Globotriaosylsphingosine or Lyso-Gb3 may also be a Fabry-related offending metabolite and may be increased in urine of Fabry patients and patients with cardiac disease.[2]

The present inventors therefore screened a large population of patients with a variety of cardiac abnormalities for Fabry disease. These cardiac patients are screened using urinary Gb3 (known to be elevated in Fabry disease), α-galactosidase A activity in blood and sequencing of GLA gene (the gene of Fabry disease).

The inventors found that patients with cardiac disease have higher than expected urinary Gb3 even though they do not have mutations in the GLA gene (are not Fabry disease patients) suggesting that Gb3 and its metabolism are involved in cardiac disease in general. The Gb3 abnormality is associated with lower than normal α-galactosidase A activity and possibly non-disease causing sequence variation of the GLA gene. The non-genetic variations in α-galactosidase A enzymatic activity that may be associated with elevated Gb3 in organs, tissue and urine can be related to: (i)

epigenetic modifications—i.e. changes in gene expression caused by mechanisms other than changes in the underlying DNA sequence—such as post-translational modifications (especially methylation but also acetylation, ubiquitylation, phosphorylation, sumoylation) or small interfering RNAs (siRNA) that can modulate transcriptional gene expression via epigenetic modulation of targeted promoters; and/or to (ii) epistatic interactions—i.e. genetic variants in one or more other genes (called modifier genes) that interact(s) with the genes encoding the lysosomal enzymes. Other yet undetermined mechanisms not related to α-galactosidase A enzymatic activity may play a role.

Over 20% of the first 220 unselected adult patients with a variety of acquired cardiac abnormalities (including coronary artery disease, arrhythmia, conduction blocks and valvular disease) had elevated urinary Gb3 levels. Upper limit of normal is considered 200 ng/ml of Gb3. Three patients had level higher than 1000 (5 times upper limit of normal). Thus far, in the patients tested, elevated Gb3 levels have not been associated with pathogenic mutations in the GLA gene. When the distribution of urinary Gb3 levels in the cardiac and healthy control populations are compared, it is clear that the cardiac population is significantly different from the healthy controls.

Method for Assay of Urinary Globotriaosylceramide: The present inventors employed Ultra Performance Liquid Chromatography (UPLC) tandem mass spectrometry (MS/MS) for quantitative determination of globotriaosylceramide (Gb3) isoforms with different fatty acid components in urine dried on filter paper cards. One milliliter of urine dried on a 5×5 cm square of filter paper is extracted with methanol using C17-Gb3 as internal standard. Ten microliters are injected into an Acquity UPLC for chromatographic separation of Gb3 isoforms using a fast methanol/water gradient with a C8 BEH, 1×50 mm, 1.7 μm UPLC column at 60° C., with a total run time of 3 minutes, including column re-equilibration. Gb3 is analyzed with a Quattro Premier MS/MS using positive electrospray ionization. Multiple reaction monitoring transitions are m/z 1060→898 for C17-Gb3 internal standard and m/1046→884, 1074→912, 1102→940, 1128→966, 1130→968, 1156→994, 1158→996, 1174→1012 to encompass eight major Gb3 isoforms. The peak areas of the MRM chromatograms for the isoforms are used with standard curves to calculate nanograms of Gb3 per ml of urine.

Figure 1B:
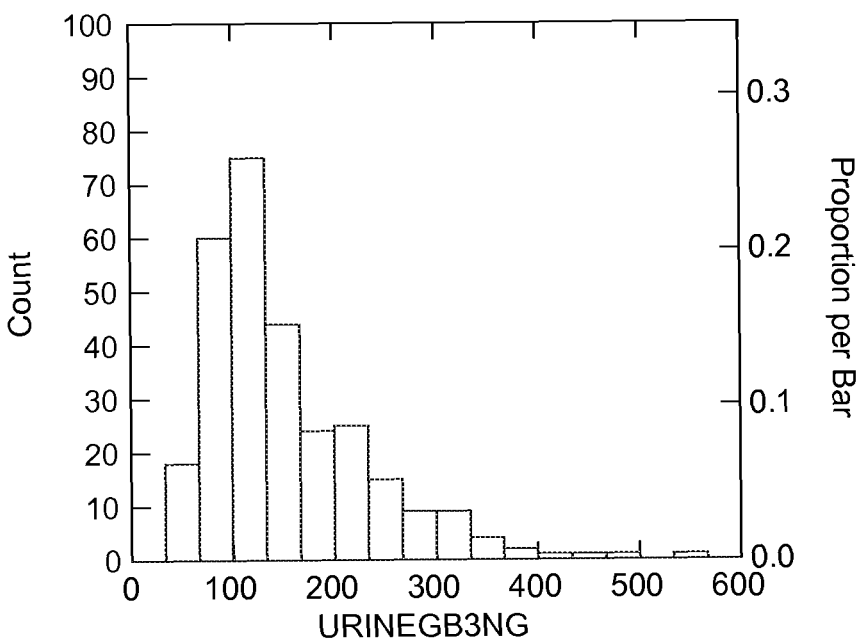
FIG. 1B is a graph showing the concentration distribution of Gb3 in the patient set shown in FIG. 1A, but the outliers (Gb3>700 ng/card) were excluded in order to clearly show the concentration distribution.

Urine specimens of cardiac patients enrolled in the study were analyzed with the software Systat results are summarized in FIG. 1A and expressed as ng of Gb3/card (mL of urine). Results for patients with levels less than 700 ng/ml were plotted as shown in FIG. 1B and shown in Table 1.

TABLE 1

Statistical analysis of patients having urinary Gb3 levels <700 ng/mL.

|  | ng/ml |
| --- | --- |
| N of cases | 220 |
| Minimum | 37.000 |
| Maximum | 84.000 |
| Range | 447.000 |
| Median | 129.500 |
| Mean | 150.077 |
| Standard Dev | 77.486 |
| C.V. | 0.516 |
| Method = CLEVELAND | |
| 1% | 37.000 |
| 5% | 63.000 |

TABLE 1-continued

Statistical analysis of patients having urinary Gb3 levels <700 ng/mL.

|  | ng/ml |
| --- | --- |
| 10% | 75.000 |
| 20% | 90.000 |
| 25% | 94.500 |
| 30% | 105.500 |
| 40% | 117.000 |
| 50% | 129.500 |
| 60% | 145.500 |
| 70% | 166.000 |
| 75% | 174.000 |
| 80% | 204.000 |
| 90% | 260.500 |
| 95% | 315.000 |
| 99% | 426.000 |

Figure 2:
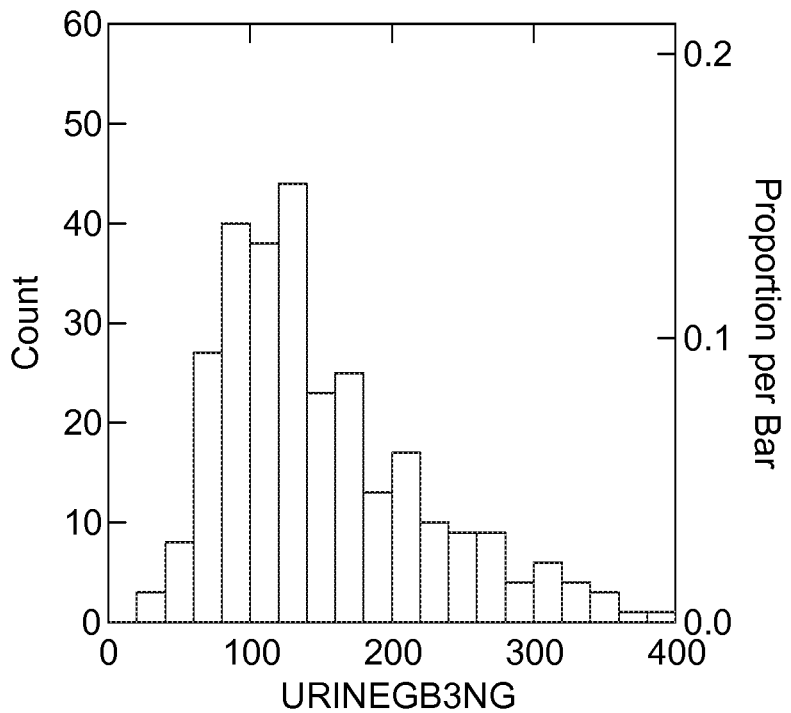
FIG. 2 is a plot showing the concentration distribution of Gb3 in the same patient set, but limited to patients with Gb3<400 ng/card in order to clearly show the concentration distribution.

Results for patients with levels less than 400 ng/ml were plotted as shown in FIG. 2 and the statistical analysis is shown in Table 2.

TABLE 2

Statistical analysis of patients having urinary Gb3 levels <400 ng/mL.

|  | ng/ml |
| --- | --- |
| N of cases | 217 |
| Minimum | 37.000 |
| Maximum | 367.000 |
| Range | 330.000 |
| Median | 129.000 |
| Mean | 145.940 |
| Standard Dev | 69.397 |
| C.V. | 0.476 |
| Method = CLEVELAND | |
| 1% | 37.000 |
| 5% | 62.700 |
| 10% | 75.000 |
| 20% | 89.900 |
| 25% | 94.000 |
| 30% | 105.000 |
| 40% | 117.000 |
| 50% | 129.000 |
| 60% | 144.000 |
| 70% | 163.800 |
| 75% | 172.000 |
| 80% | 200.100 |
| 90% | 255.600 |
| 95% | 290.000 |
| 99% | 349.620 |

Figure 3:
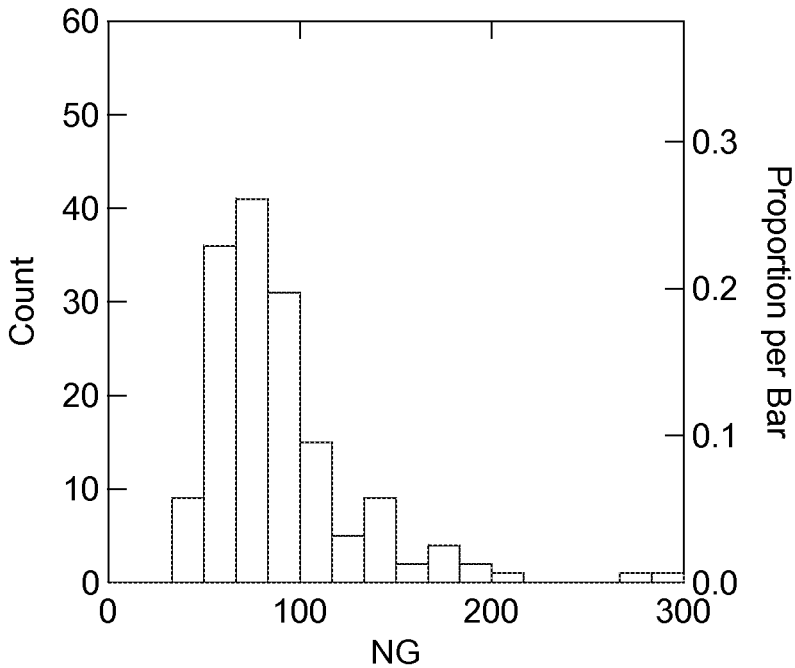
FIG. 3 is a graph showing the concentration distribution of Gb3 in normal control population (N=157)
Figure 4:
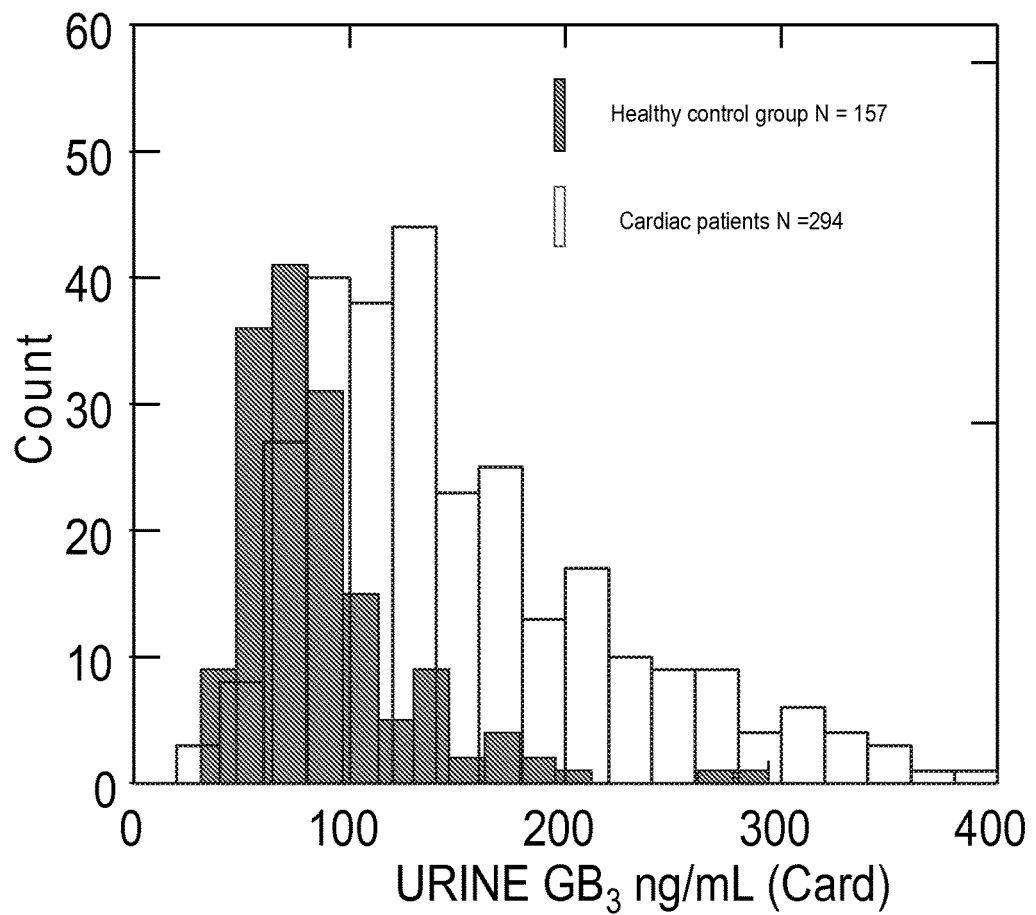
FIG. 4 is a combination plot the Gb3 concentration distribution in healthy controls (N=157) and cardiac patients (N=294).

Gb3 levels in the normal population (N=157) is shown in FIG. 3. FIG. 4 is a combination plot showing the results obtained for the cardiac population (N=294) and the healthy control group (N=157).

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Pat. No. 7,445,886: Macrophage migration inhibitory factor as a marker for cardiovascular risk.
U.S. Patent Application No. 20040132688: Plasma glucosylceramide deficiency as risk factor for thrombosis and modulator of anticoagulant protein C.
[1] http://www.medicalnewstoday.com/articles/71159.php
[2] Johannes M. Aerts, Johanna E. Groener, Sijmen Kuiper, Wilma E. Donker-Koopman Anneke Strijland, Roelof Ottenhoff, Cindy van Roomen, Mina Mirzaian, Frits A. Wijburg, Gabor E. Linthorst, Anouk C. Vedder, Saskia M. Rombach, Josanne Cox-Brinkman, Pentti Somerharju‡, Rolf G. Boot, Carla E. Hollak, Roscoe O. Brady, and Ben J. Poorthuis, (2008), "Elevated globotriaosylsphingosine is a hallmark of Fabry disease", *PNAS*, 105(8), 2812-2817.

What is claimed is:

1. A method of treating a cardiac disease or condition in a non-Fabry disease subject comprising administering to the subject in need thereof an effective amount of 1-deoxygalactonojirimycin or a salt thereof, wherein the subject does not have Fabry disease.

2. The method of claim 1, wherein the 1-deoxygalactonojirimycin or a salt thereof is administered in an amount to yield a Gb3 concentration in the urine of the subject of 200 ng/ml of lower.

3. The method of claim 1, wherein 1-deoxygalactonojirimycin hydrochloride is administered.

4. The method of claim 1, wherein the subject has no genetic predisposition towards Fabry disease.

5. The method of claim 1, wherein the subject is a non-Fabry disease cardiac patient.

6. The method of claim 1, wherein the cardiac disease or condition is selected form hypertrophic cardiomyopathy, cardiac rhythm and conduction defects, coronary artery disease, arrhythmia, conduction blocks and valvular disease.

7. The method of claim 3, wherein the subject has no genetic predisposition towards Fabry disease.

* * * * *

UNITED STATES PATENT AND TRADEMARK OFFICE
CERTIFICATE OF CORRECTION

PATENT NO. : 9,750,732 B2
APPLICATION NO. : 14/729630
DATED : September 5, 2017
INVENTOR(S) : Schiffmann et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 27 days.

Signed and Sealed this
Nineteenth Day of June, 2018

Andrei Iancu
*Director of the United States Patent and Trademark Office*